United States Patent [19]

Teumim-Stone

[11] Patent Number: 5,090,908
[45] Date of Patent: Feb. 25, 1992

[54] LASER APPARATUS FOR PERIODONTAL TREATMENT

[76] Inventor: Zvi Teumim-Stone, Ramot 01 36/26, Jerusalem, Israel

[21] Appl. No.: 376,102

[22] Filed: Jul. 6, 1989

[30] Foreign Application Priority Data

Jul. 6, 1988 [IL] Israel .......................... 87015

[51] Int. Cl.$^5$ ................................. A61C 5/00
[52] U.S. Cl. ............................. 433/215; 433/229; 606/17
[58] Field of Search ............. 433/29, 159, 215, 229; 128/396, 397, 398; 606/11, 13, 14, 17

[56] References Cited

U.S. PATENT DOCUMENTS

| | | | |
|---|---|---|---|
| 4,470,414 | 9/1984 | Imagawa et al. | 606/11 |
| 4,764,114 | 8/1988 | Jeffcoat et al. | 433/120 X |
| 4,784,135 | 11/1988 | Blum et al. | 606/3 |
| 4,826,431 | 5/1989 | Fujimura et al. | 433/215 X |
| 4,842,390 | 6/1989 | Sottini et al. | 606/15 X |
| 4,852,567 | 8/1989 | Sinofsky | 606/15 X |

FOREIGN PATENT DOCUMENTS

| | | | |
|---|---|---|---|
| 0070459 | 1/1983 | European Pat. Off. | 606/17 |
| 2550693 | 5/1977 | Fed. Rep. of Germany | 606/13 |
| 3413520 | 10/1985 | Fed. Rep. of Germany | 606/13 |
| 2044104 | 10/1980 | United Kingdom | 128/398 |

*Primary Examiner*—Robert P. Swiatek
*Assistant Examiner*—Nicholas D. Lucchesi
*Attorney, Agent, or Firm*—Browdy and Neimark

[57] ABSTRACT

An improved laser apparatus for periodontal treatment comprising a surgical laser and a handpiece for focussing the beam of laser light and directing it on to tissue within a periodontal pocket. The improvement comprises a protective shield at the end of the handpiece displaceable from a first position preventing the passage of the laser beam to a second position allowing the laser beam to pass. Preferably, the protective shield includes two prongs located at the end of the handpiece and capable of relative lateral displacement thereby providing the effect of an improved laser scalpel.

11 Claims, 3 Drawing Sheets

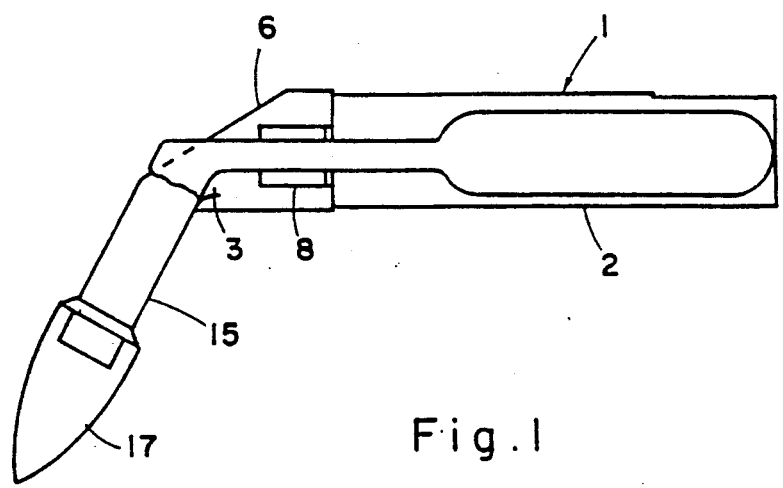
Fig.1
Fig.2
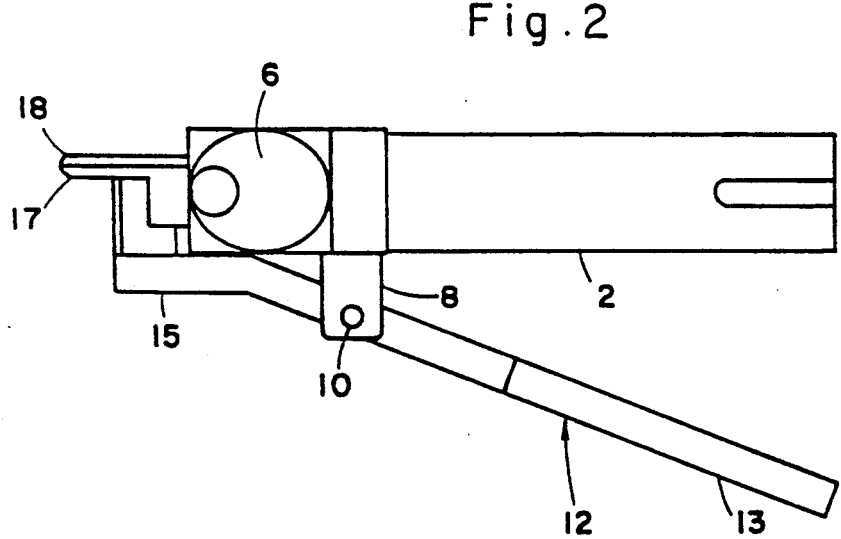
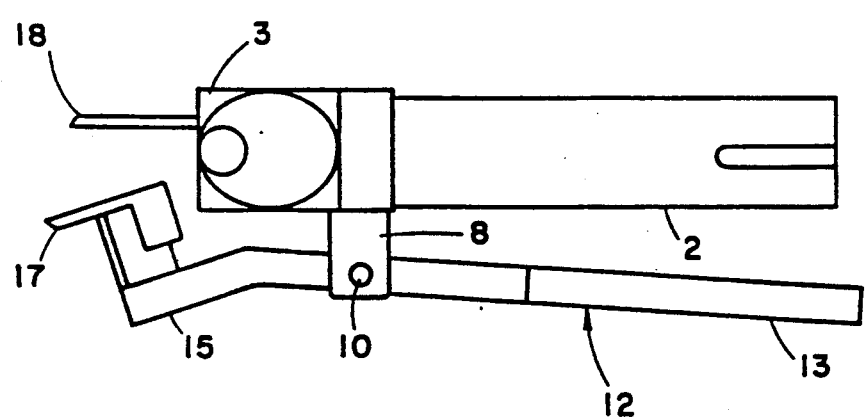
Fig.3

LASER APPARATUS FOR PERIODONTAL TREATMENT

FIELD OF THE INVENTION

This invention relates to a laser apparatus for periodontal treatment. In the context of the invention, treatment is used to refer to any appropriate periodontal procedure including surgery.

BACKGROUND OF THE INVENTION

Chronic inflammation resulting from infection of the gingiva (gum tissue) leads to a separation of these tissues from the root surfaces of the teeth, forming spaces known as "periodontal pockets". The periodontal pockets become more and more infected so that, if not treated, teeth are eventually lost because of the extensive destruction of the supporting tissue of the teeth.

In order to stop this destructive process and prevent loss of teeth, the periodontal pockets and the infected tissue therein must be eliminated. Formerly this required a surgical procedure known as a "gingivectomy" in which the entire infected gum margin is cut away. In recent years, the technique has been modified owing to the inaesthetic appearance and tooth sensitivies most often resultant with such an approach. Currently, the periodontal pockets are surgically opened so as to provide access to the infected tissues therein. These tissues are surgically removed and the gum margins are closed again so as to contact the tooth surfaces in such a manner that, after guided healing, no periodontal pocket nor associated infection remain.

Prior art periodontal surgery suffers from a number of drawbacks. There is frequently significant bleeding which impedes the surgeon's vision. The operation requires the provision of a local anaesthetic for pain control, resulting in post-operative pain and swelling to the patient. Additionally, an antibiotic cover must generally be provided.

In order to overcome some of these these drawbacks, surgical lasers have been employed in an attempt to provide dry, bloodless surgery which produces minimal post-operative discomfort to the patient. The use of lasers can obviate the need for a local anaesthetic and provides a sterilised field requiring no antibiotic cover. Such an approach is described, for example, in an article entitled "The Laser Gingivectomy" by Robert M. Pick et al appearing in The Journal of Periodontology, August, 1985 Vol. 56 Number 8. Pick et al employ a $CO_2$ laser with some success to avoid some of the problems described above relating to the surgical gingivectomy.

The $CO_2$ laser used by Pick et al is a surgical laser as opposed to high power industrial lasers and so-called "soft medical lasers". The latter are relatively low power lasers which are employed in laser therapy applications, as opposed to surgical lasers which are intended for cutting through tissue and for destroying diseased tissue by vaporisation thereof.

However, the approach used by Pick et al suffers from a number of drawbacks, due in part to the limitations of the laser apparatus employed. Thus, no protective shielding is provided for the laser and, therefore, extreme caution must be taken during its use. Furthermore, the laser employed by Pick et al is not adapted physically to touch the infected tissue and therefore provides no tactile feedback to the surgeon. This contrasts with standard surgical procedures using scalpels and renders the laser apparatus described by Pick et al relatively difficult to use.

The use of lasers per se in dentistry is described in a paper entitled "Basic Researches and Clinical Applications in Oral Surgery of Nd-YAG Laser with Handpieces Designed for Dentistry" by Takumi Sato et al, and appearing in The Journal of Japan Society for Laser Medicine, Vol. 5, No. 3: 405-408, 1985.

Sato et al describe a Nd-YAG laser apparatus specially adapted for dental use and suitable for the laser gingivectomy, similar to that performed by Pick et al with the $CO_2$ laser. The handpiece in the Nd-YAG laser is terminated in a sapphire tip coincident with a focussed laser beam, so that the laser cuts through tissue at its point of contact therewith. However, the apparatus described by Sato et al is suitable for external use only as are hitherto proposed $CO_2$ laser handpieces. Neither is able to perform the more extensive procedures associated with periodontal surgery, demanding opening the periodontal pocket, as outlined above.

SUMMARY OF THE INVENTION

It is an object of the invention to provide a laser apparatus for periodontal treatment, in which many of the drawbacks associated with the prior art are significantly reduced or eliminated.

According to the invention there is provided in a laser apparatus for periodontal treatment, comprising:

a surgical laser for producing a beam of laser light, and a handpiece coupled to the laser and containing: directing means for directing the laser beam as a focussed beam on to tissues within a periodontal pocket;

the improvement whereby there is further provided:

a protective shield at an end of the handpiece displaceable from a first position preventing passage of the laser beam to a second position allowing the laser beam to pass therethrough, and displacing means coupled to the shield for displacing the shield relative to the handpiece from the first position to the second position.

Thus, the laser apparatus according to the invention includes the provision of a displaceable protective shield which normally prevents passage of the laser beam but may be displaced during use so as to let the laser beam pass to the infected areas. Preferably, the protective shield comprises a mechanical arrangement including two prongs located at the end of the laser handpiece and normally in contact with each other. In this position, the laser beam is prevented from passing therethrough.

A lever is provided on the laser handpiece so as to be easily accessible to the surgeon and permits the prongs to be laterally displaced with respect to each other, thereby allowing the laser beam to pass. Such an arrangement ensures that no laser light is emitted from the end of the laser handpiece until the surgeon operates the lever.

In the preferred embodiment, the prongs may be introduced by the surgeon to the base of the pocket space between the diseased pocket wall and the corresponding tooth, such that operation of the lever in order to allow passage of the laser beam will, at the same time, expand the periodontal pocket. This allows the surgeon to direct the laser beam to the base of the periodontal pocket so as to cut tissue therein. Until the pocket is sufficiently wide for him to see where exactly to cut, the surgeon will exploit the tactile feedback resulting from the contact of the shield with the severed tissue.

BRIEF DESCRIPTION OF THE DRAWINGS

The invention will now be described with regard to a laser apparatus for periodontal treatment and with reference to the accompanying drawings, in which:

FIGS. 1, 2 and 3 are pictorial representations showing three views of a first embodiment according to the invention.

DETAILED DESCRIPTION OF PREFERRED EMBODIMENTS

Figure 4:
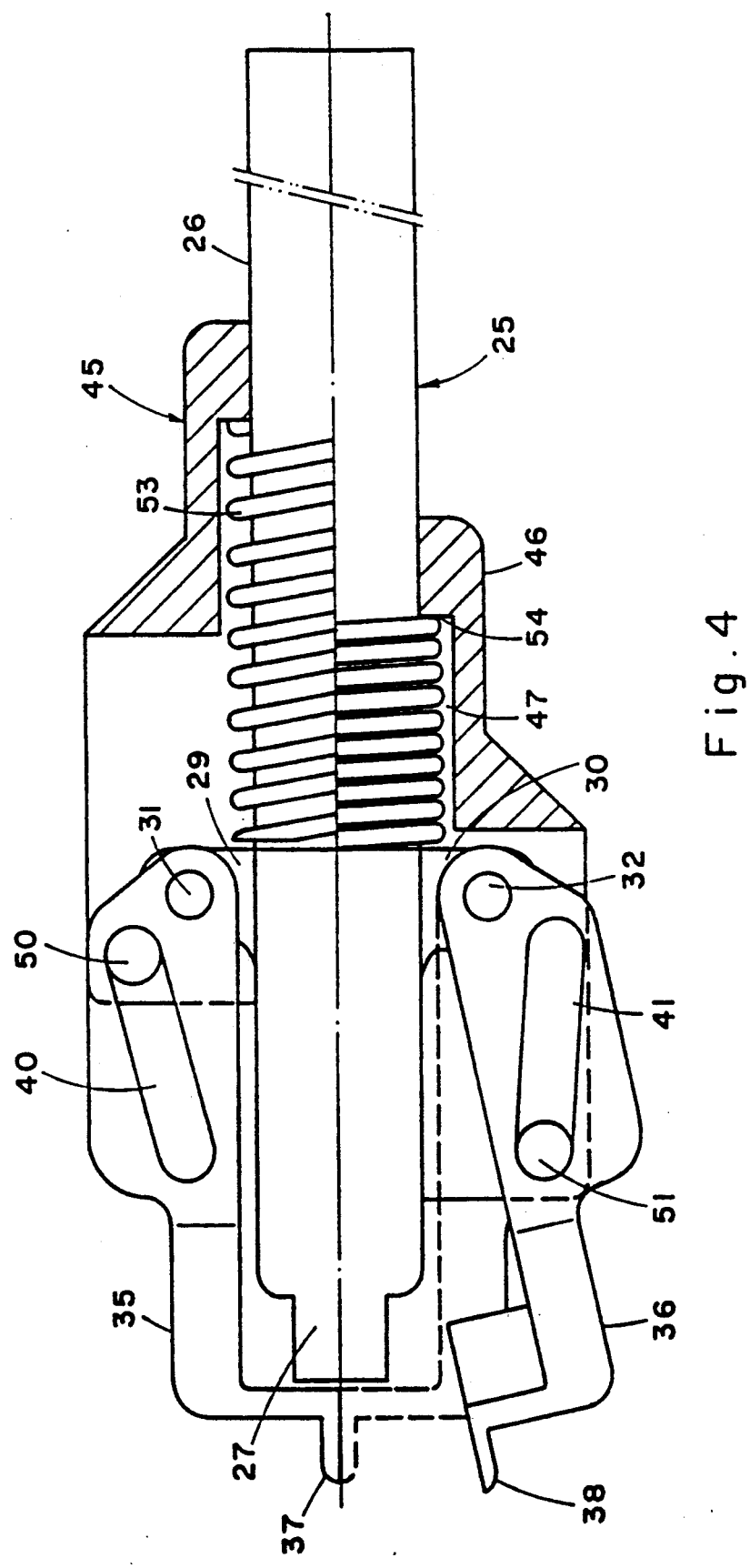
FIG. 4 is a pictorial representation of a second embodiment according to the invention.

Referring to FIG. 1 there is shown a handpiece 1 for a $CO_2$ surgical laser (not shown) adapted for periodontal treatment. The handpiece 1 is provided with a body portion 2 coupled to the laser and terminating in a head unit 3 set an angle of 45° to the body portion 2. The laser produces a beam of laser light (not shown) which is directed towards the body portion 2 of the handpiece 1 by a series of mirrors (not shown) housed within an arm assembly (not shown) as provided in conventional dental units. The laser beam within the handpiece 1 is reflected by a mirror 6 placed in the path of the laser beam equiangularly between the body portion 2 and the head unit 3. The mirror 6 thus constitutes a directing means for directing the laser beam along the axis of the head unit 3. Associated with the laser is a lens (not shown) for producing a focussed beam at the end of the head unit 3.

Protruding from the body portion 2 is a U-shaped bracket 8, shown more clearly in FIGS. 2 and 3. Through both sides of the bracket 8 there are provided apertures 10, which accommodate a pivot (not shown) for pivotally supporting a lever 12 with respect to the body portion 2. The lever 12 comprises a handle portion 13 adjacent to the body portion 2 and is connected to a jaw 15 at its lower end adjacent to the head unit 3.

Releasably inserted into the jaw 15 is a first prong 17 whilst a second prong 18 is releasably inserted into the head unit 3 in a direction substantially parallel to its axis. The two prongs 17 and 18 are made of a thermally insulating material such as plastics and are provided at their free ends with points adapted to be inserted, if required, into the space between the wall a of diseased periodontal pocket and the respective tooth. The lever 12 may be pivotally rotated from a first position, shown in FIG. 2, wherein the two prongs 17 and 18 are in contact with each other to a second position shown, in FIG. 3 wherein they are displaced apart. The prongs 17 and 18 will generally be constituted by a system of dental tools having various shapes, as described in greater detail below with reference to FIGS. 5, 6 and 7 of the drawings, and specially adapted for different dental procedures. The surgeon will thus insert different prongs into the jaw 15 and the head unit 3 according to his requirements.

The operation of the prongs 17 and 18 is as follows. With the lever 12 in the first position shown in FIG. 2, the end of the head unit 3 is covered and consequently the laser beam is prevented from passing therethrough. When the lever 12 is rotated to the second position shown in FIG. 3, the end of the head unit 3 is exposed and the laser beam is therefore able to pass. The prongs 17 and 18 thus constitute a protective shield at the end of the handpiece 1 preventing the passage of the laser beam until required by the surgeon. The lever 12 constitutes a displacing means coupled to the protective shield for displacing the latter relative to the handpiece 1.

The protective shield not only prevents passage of the laser beam until required by the surgeon, but it also protects crown and root surfaces of the tooth from exposure to the laser beam once the shield has been displaced relative to the handpiece 1.

The prongs 17 and 18 may further be inserted into the space between a diseased pocket wall and the corresponding tooth. When this is done, the action of rotating the lever 12 into the second position wherein the prongs 17 and 18 are displaced apart, also expands the periodontal pocket. This provides greater access to the surgeon and permits him to direct the laser beam to the point of contact of the tissue with the base of the periodontal pocket. This feature enables the laser to be used internally as well as externally.

Referring to FIG. 4, there is illustrated a second embodiment according to the invention relating to a handpiece shown generally as 25 for a $CO_2$ surgical laser (not shown). The handpiece 25 includes a body portion 26 terminating in a head unit 27. The laser emits a beam of laser light which is directed towards the body portion 26 in a similar manner to that provided for in the first embodiment as described above with reference to FIGS. 1 to 3 of the drawings. A lens (not shown) is provided within the head unit 27 for focussing the beam of laser light.

Protruding from each side of the body portion 26 are a pair of generally U-shaped brackets 29 and 30 provided with apertures 31 and 32 in both their flange portions, which accommodate a pivot (Not shown) for pivotally supporting a pair of jaws 35 and 36 in each of the brackets 29 and 30, respectively. The jaws 35 and 36 are generally L-shaped with apertures (not shown) being formed near the end of the vertical section of the L for accommodating the corresponding pivot. Provided at the end of the horizontal section of the L in each jaw 35 and 36 is a prong 37 and 38, respectively, each of which is made of a thermally insulating material and is pointed at its free end for the reason explained above with reference to the first embodiment.

The jaws 35 and 36 are adapted to rotate about their respective pivots from a first position, in which the prongs 37 and 38 are in contact with each other, to a second position in which they are laterally displaced apart. In the first position, both jaws 35 and 36 assume the orientation of the jaw 35 as shown in FIG. 4, whilst in the second position, they assume the orientation of the jaw 36 as shown in FIG. 4. However, it will be understood that the disparate positions of the two jaws 35 and 36 as shown in FIG. 4 are for the sake of illustration only. In reality, both jaws 35 and 36 are adapted to rotate about their respective points symmetrically.

The vertical section of each L-shaped jaw 35 and 36 is made sufficiently wide to accommodate a slot 40 and 41, respectively, sloping inwardly from the pivotally supported end of the jaw 35 and 36 toward its free end. Surrounding the body portion 26 is a plunger assembly 45 which is capable of relative axial displacement with respect to the body portion 26. The plunger assembly 45 includes a handle portion 46 having an internal axial bore 47. The plunger assembly 45 flares outward from the handle portion 46 such that its ultimate width is approximately the same as that of the jaws 35 and 36 at their point of pivotal coupling with the body portion 26.

Protruding from opposite sides of the plunger assembly 45 in line with the end of the slots 40 and 41 nearest to it, is a pair of bolts 50 and 51 each of which slidingly engages a corresponding slot 40 and 41. The plunger assembly is axially displaceable with respect to the body portion 26 such that the bolts 50 and 51 are adapted to slide within the respective slots 40 and 41. A compression spring 53 is provided within the axial bore 47 engageable on an inside surface 54 of the handle 46 and the flanges 29 and 30.

The operation of the apparatus is as follows. As the plunger assembly 45 is depressed against the action of the compression spring 53, the locus of each bolt 50 and 51 is constrained to lie along a straight line parallel to the axis of the body portion 26. Consequently, the locus of the point of contact of the slots 40 and 41 with the corresponding bolts 31 and 32 must also lie along the same straight line. Thus, as the plunger assembly 45 is displaced towards the head unit 27, the jaws 35 and 36 are rotatably displaced about their respective pivots in such a manner as to expose the head unit 27 and allow the laser beam to pass therethrough.

The compression spring 53 constitutes a spring biasing means for ensuring that when pressure on the plunger assembly 45 is released, the jaws 35 and 36 will return to their closed position.

The embodiment described with reference to FIG. 4 may be used for external surgical procedures, the jaws 35 and 36 functioning as a displaceable protective shield for preventing passage of the laser beam until required. Alternatively, the provision of the pointed prongs 37 and 38 renders the handpiece 25 equally suitable for internal surgery, whereby the prongs 37 and 38 may be inserted into the space between a diseased pocket wall and the corresponding tooth. Depression of the plunger assembly 45 will then act to expand the periodontal pocket, whilst at the same time exposing the head unit 27 and allowing the laser beam to pass therethrough.

It is a preferred feature of both the embodiments described above that the surgeon be provided with tactile feedback when using the handpiece. In a $CO_2$ laser, this may be achieved by focussing the laser beam at the end point of the protective shield, so that the point of contact of the protective shield with the tissue determines the point of laser cutting action. Alternatively, when employing a Nd-YAG laser having a sapphire tip, it is a characteristic design feature that the point of focus of the laser beam is at the end of the sapphire tip. Consequently, any tissue contacted by the sapphire tip is cut by the Nd-YAG laser. It is therefore preferable when employing a Nd-YAG laser, to locate the protective shield such that its point is coincident with the end of the sapphire tip.

Thus, in a surgical laser having a handpiece according to the invention, the laser will cut through tissue actually contacted by the tip of the protective shield. Alternatively, the laser may be withdrawn slightly from an area of diseased tissue so that the laser beam incident on the tissue will be defocussed. The laser will then destroy the diseased tissue by vaporising it. When used in the cutting mode, the surgeon experiences a similar sensation to that obtained when using a scalpel, even when the point of contact of the laser is not visible to him, and it is this sensation which is referred to as "tactile feedback".

Figure 5:
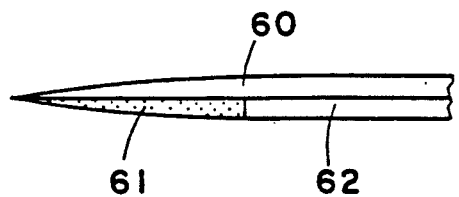
FIGS. 5, 6 and 7 are pictorial representations of various sapphire tip arrangements which may be employed in a Nd-YAG laser according to either of the preferred embodiments.
Figure 6:
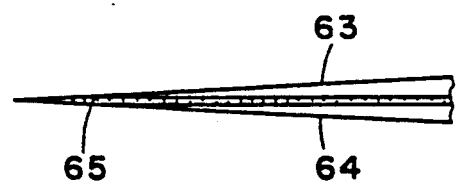
Figure 7:
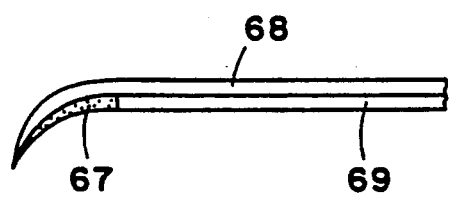

Referring to FIGS. 5, 6 and 7, there are shown specially adapted sapphire tips which may be provided for use with a Nd-YAG laser, in order to provide tactile feedback whilst, at the same time, allowing the laser beam to be shielded in accordance with the invention. In the Nd-YAG laser, the laser beam is directed along an optical fibre to the end of sapphire tip is thus coincident with the focussed beam. In order to shield healthy tissue from the laser beam in accordance with the invention, a protective shield is fused to the sapphire tip.

FIG. 5 shows one variation wherein a protective shield 60 is fused to one side of the sapphire tip 61 so that the area to one side of the sapphire tip 61 is permanently shielded. The sapphire tip 61 is so fused to the protective shield 60 that the end of the sapphire tip 60 and the tip of the protective shield 60 are substantially coincident. The laser beam is directed to the sapphire tip 61 via an optical fibre 62 such that the laser beam is brought to a focus at the end of the sapphire tip 61. The single shield sapphire tip will effectively duplicate the action of a standard steel scalpel in terms of both feel and versatility. It is thus equally well adapted for entering a pocket space without expanding it, dissecting and/or cutting the contacted tissues and also for performing line incisions. Additionally, the shield provides means for separating the tissues thus treated.

In FIG. 6 an alternative variation is shown wherein a protective shield comprising first and second portions 63 and 64, respectively, is provided in a manner similar to that described above with reference to FIGS. 1 to 4 of the drawings. The first portion 63 of the protective shield is fused to a sapphire tip 65 as described above with reference to FIG. 5. The second portion 64 of the protective shield is displaceable with respect to the first portion 63 so as to cover or expose the sapphire tip 65 according to the requirements of the surgeon. This variation allows the surgeon to expand the periodontal pocket for providing greater access therein, as described above with reference to FIGS. 1 to 4 of the drawings.

FIG. 7 shows a third variation wherein a curette having a sapphire tip 67 is fused to a protective shield 68 thereby permitting a laser in accordance with the invention to be used when required for duplicating the action of a standard steel curette. An optical fibre 69 directs the laser beam to the sapphire tip 67 coincident with the focussed beam, as explained above with reference to FIG. 5.

The protective shield in accordance with the preferred embodiments not only shields healthy tissue from the laser beam, but it also protects crown and root surfaces of the tooth from exposure to the laser beam. Additionally, the protective shield enables the handpiece to emulate the feel of a periodontal steel scalpel, both providing "tactile feedback" to the surgeon and permitting him physically to move tissue which has been cut by the laser.

I claim:

1. In a laser apparatus for periodontal treatment, comprising:
    a surgical laser for producing a beam of laser light, and
    a handpiece coupled to the laser and containing:
    directing means for directing the laser beam as a focused beam on to tissues within a periodontal pocket;
    the improvement whereby there is further provided:

a protective shield at an end of the handpiece shaped and dimensioned for insertion into a periodontal pocket and displaceable from a first position preventing passage of the laser beam to a second position allowing the laser beam to pass therethrough, and displacing means coupled to the shield for displacing the shield relative to the handpiece from the first position to the second position.

2. The improvement according to claim 1, wherein the shield includes:

two prongs located at the end of the handpiece and capable of relative lateral displacement, such that in said first position the prongs are in contact with each other and in said second position the prongs are displaced apart;

said displacing means being coupled to at least one of the prongs.

3. The improvement according to claim 2, wherein the two prongs are adapted for insertion into the base of the pocket space between a diseased pocket wall and the corresponding tooth, whereby operation of the displacing means expands the periodontal pocket.

4. The improvement according to claim 1, wherein there are further provided spring biasing means coupled to the displacing means for biasing the protective shield into the first position.

5. The improvement according to claim 1, wherein there is further provided:

at least one pivot rigidly connected to the handpiece, and two jaws, at least one of which is pivotally coupled to the handpiece about said at least one pivot, so as to be relatively displaceable from the first position to the second position.

6. The improvement according to claim 5, wherein the displacing means is constituted by a lever coupled to said at least one jaw and pivoted at an intermediate point thereof to the handpiece.

7. The improvement according to claim 5, wherein the displacing means is constituted by a plunger assembly articulatedly coupled to said at least one jaw and axially displaceable with respect to the handpiece.

8. The improvement according to claim 7, wherein each one of said at least one jaw is provided with a slot sloping inwardly from the pivotally coupled end of the jaw towards the free end of the jaw and slidably engageable with a bolt provided on the plunger assembly, whereby axial displacement of the plunger assembly is adapted to rotate the jaw about the corresponding pivot.

9. The improvement according to claim 1, further including optical means for focussing the laser beam at a point on the protective shield, whereby in use said tissues are adapted to be cut when contacted by said point.

10. The improvement according to claim 1, wherein the directing means includes an optical fiber having a first end for receiving the laser beam and a second end for emitting said focussed beam.

11. In a laser apparatus for periodontal treatment, comprising:

a surgical laser for producing a beam of laser light, and a handpiece coupled to the laser and containing:

directing means for directing the laser beam as a focussed beam on to tissues within a periodontal pocket;

the improvement whereby there is further provided:

a protective shield at an end of the handpiece displaceable from a first position preventing passage of the laser beam to a second position allowing the laser beam to pass therethrough, and displacing means coupled to the shield for displacing the shield relative to the handpiece from the first position to the second position, wherein:

the directing means includes an optical fiber having a first end for receiving the laser beam and a second end for emitting said focussed beam, the laser is a Nd-YAG laser, and a sapphire tip is fused to a point on the protective shield proximate said second end of the optical fiber;

whereby in use said tissues are cut when contacted by said point.

* * * * *